United States Patent [19]

McRae

[11] Patent Number: Plant 5,991

[45] Date of Patent: May 19, 1987

[54] ASIATIC LILY NAMED ALPENGLOW

[75] Inventor: Edward A. McRae, Boring, Oreg.

[73] Assignee: Melridge Inc., Gresham, Oreg.

[21] Appl. No.: 710,590

[22] Filed: Mar. 11, 1985

[51] Int. Cl.[4] ..... A01H 5/00
[52] U.S. Cl. ..... Plt./68
[58] Field of Search ..... Plt./68

*Primary Examiner*—James R. Feyrer
*Attorney, Agent, or Firm*—Charles W. Rummler; John B. Lungmus

[57] ABSTRACT

A new variety of hybrid Asiatic lily particularly distinguished by its large clusters of medium size flowers of a pure rose color tone which is unique in the hybrid Asiatic divisions of lilies suited to forcing and commercial cultivation, the flowers being of excellent form and long persistence both on the plant and as cut-flowers. The plant itself is highly resistant to disease, shows high tolerance to virus, and is an excellent garden plant. Also, this plant is very vigorous, is a good grower and propagator, and the bulbs may be precooled and forced for cut-flower production.

1 Drawing Figure

BACKGROUND OF THE INVENTION

My new variety of lily plant originated as a seedling resulting from my cross of a hybrid clone from a group of "Hallmark"×"Destiny" (unpatented) as the seed parent and "Juliana" (U.S. Plant Pat. No. 4,333) as the pollen parent, that crossing having been done at Sandy, Oreg., in the course of breeding efforts carried on by me since 1976 with the object of producing upright Asiatic lilies in the rose-pink color tones heretofore unknown in the lily breeding art.

This new variety of lily plant has been asexually reproduced by me and under my direction at Sandy, Oreg., and successive generations produced by bulb scale propagation and natural propagation from bulblets have demonstrated that the novel and distinctive characteristics of this new plant hold true from generation to generation and appear to be firmly fixed.

This new plant possesses all of the desired characteristics of excellence of form, color and habit, and in addition, possesses to a high degree the desirable characteristics of hybrid vigor, great hardiness and disease resistance; and additionally, the clone is a vigorous grower and a good propagator as observed at Sandy, Oreg.

DESCRIPTION OF THE DRAWING

My new variety of lily plant is illustrated by the accompanying photographic drawing which shows buds and open blooms, partially hand-painted to show the true color, and illustrating the flower form and the petal arrangement.

DESCRIPTION OF THE NEW PLANT

The following is a detailed description of my new variety of Asiatic lily as observed at Sandy, Oreg., with color designations according to The R.H.S. Colour Chart published by The Royal Horticultural Society of London, England, and with nomenclature according to The International Lily Register, 2nd edition, of The Royal Horticultural Society.

THE PLANT

Origin: Seedling.
Parentage:

*Seed parent.*—"Hallmark"×"Destiny" (unpatented).
*Pollen parent.*—"Juliana"(U.S. Plant Pat. No. 4,333).

Classification:
*Botanic.*—Hybrid Lilium cultivar, Division 1-A of Horticultural Classification of Lilies, by The Royal Horticultural Society.
*Commercial.*—Asiatic hybrid lily.

Form: Single stem, erect and stately.
Height: About 90 to 110 cm. from bulbs about 15 to 18 cm. in circumference.
Growth: Vigorous and upright.
Foliage:
*Quantity.*—Abundant.
*Size of leaf.*—About 7 to 11 cm. long.
*Shape of leaf.*—Short with acuminate apex and entire margins.
*Texture.*—Leathery.
*Aspect.*—Glossy.
*Color.*—Medium green on both upper and under sides and slightly pubescent along the margins.

Bulbs:
*Size.*—Ranging up to about 25 cm. in circumference for commercial use.
*Color.*—White.

THE BUD

Form: Long ovoid with obtuse tip end.
Size: About 7.5 cm. long and about 5 to 6 cm. in circumference increasing as bud develops.
Opening rate: The bud opens slowly.
Color: Pure rose when outer tepals first divide.
Tepals when unfurling:
*Color.*—Pure rose on both inside and outside surfaces.
Peduncle: About 7.5 to 10 cm. long.
*Character.*—Generally erect.
*Color.*—Dark green with reddish tinge.

THE FLOWER

Blooming habit: Annually, once and profusely, in mid-season for Asiatic lilies.
Size: Large; about 14 to 17 cm. in diameter.
Borne: In clusters of about 6 to 8 on a single stem.
Shape: Generally flat.

Tepalage:

*Number.*—Six.

*Arrangement.*—Imbricated.

*Shape.*—Generally ovate with long outer end portions terminating in an acute apex and having entire margins.

*Appearance.*—Shiny.

*Color.*—Pure rose, generally R.H.S. 48 B-C; the flower color is deepest at the tips, shading to a slightly softer color toward the center of the flower and having an almost imperceptible flush of soft yellow-gold underlying the soft pink at the center of the flower.

*Color change.*—As the flower ages, the color fades to a more purplish rose (R.H.S. 62 A-B).

*Maculation.*—The tepals are copiously maculate with small spots of deep magenta color.

Persistence: Tepals stay on the stem about three weeks.

Fragrance: The flowers are sometimes lightly scented.

Disease resistance: The flower and plant are resistant to disease; in particular, Fusarium and Botrytis.

Lasting quality: The flower is long lasting both on the plant and as a cut flower.

REPRODUCTIVE ORGANS

Stamens:

*Number.*—Six.

*Arrangement.*—Typical of Asiatic lilies.

Filaments:

*Length.*—About 5 cm.

*Color.*—Ivory or light green.

Pollen:

*Color.*—Greyed red (R.H.S. 172 A-B).

Pistils:

*Number.*—One.

*Style length.*—About 5 cm.

Stigma color: Deep purple.

Character of ovaries: Typical of genus Lilium.

THE FRUIT

Fertility: The fruit is fertile.

Shape: Ovoid

Color at maturity: Soft brown.

This new variety of hybrid Asiatic lily most nearly resembles the variety "Twilight" (U.S. Plant Pat. No. 4,179), but has upright rather than side facing flowers, short pedicels, and a high bud count. Also, it has a broader tepalled flower form and has green rather than reddish green stems. I claim:

1. A new and distinct variety of Asiatic hybrid lily plant, substantially as herein shown and described, characterized in particular by its unique pure rose color tone and the excellence of its flower form; its vigorous growth and propagation characteristics; and its high resistance to disease and tolerance to virus.

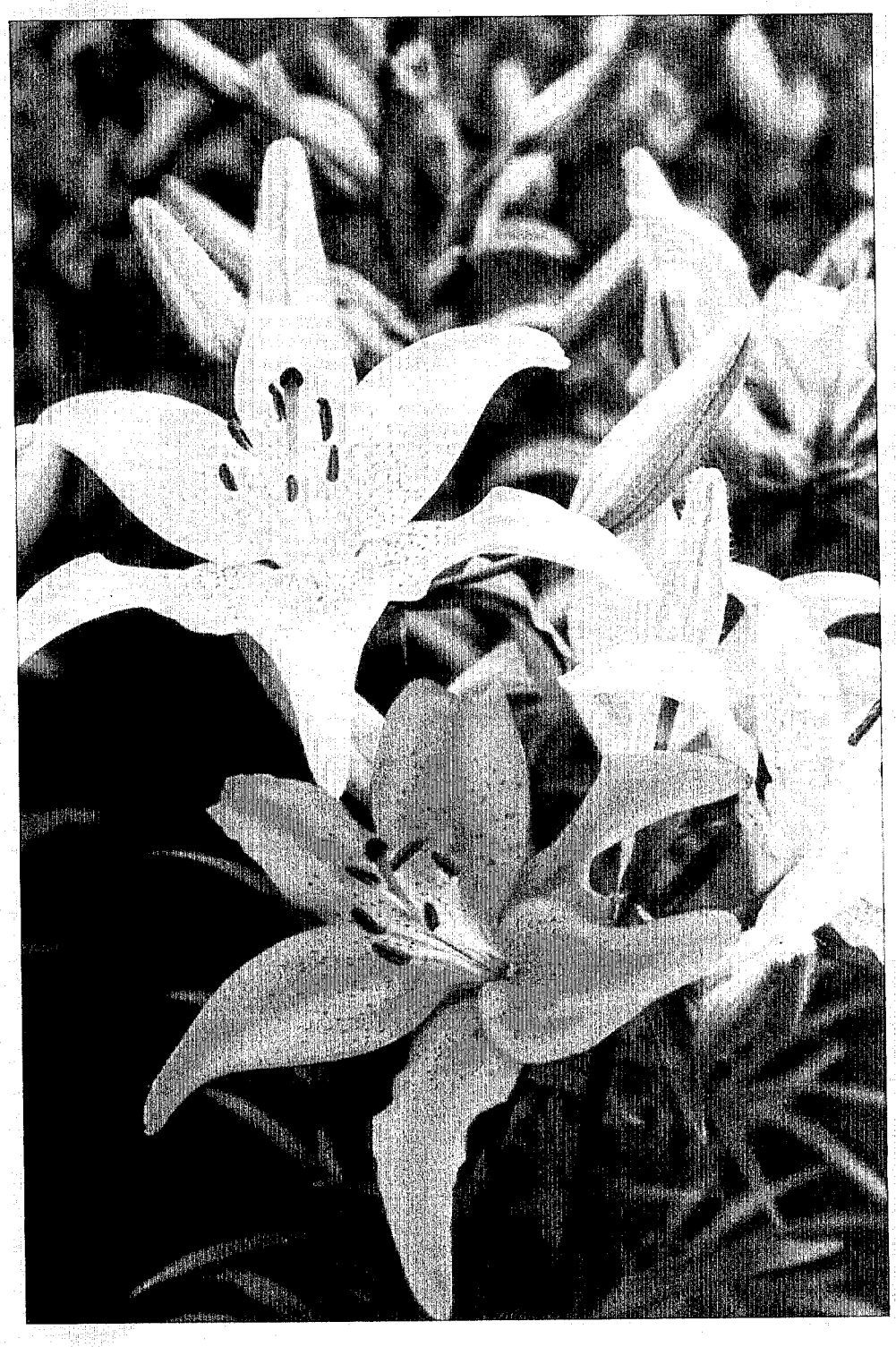

* * * * *